United States Patent
Nakatou et al.

(10) Patent No.: US 10,088,448 B2
(45) Date of Patent: Oct. 2, 2018

(54) GAS SENSOR ELEMENT

(71) Applicant: DENSO CORPORATION, Kariya, Aichi-pref. (JP)

(72) Inventors: Mitsunobu Nakatou, Chiryu (JP); Keigo Mizutani, Okazaki (JP); Takashi Araki, Kariya (JP)

(73) Assignee: DENSO CORPORATION, Kariya (JP)

( * ) Notice: Subject to any disclaimer, the term of this patent is extended or adjusted under 35 U.S.C. 154(b) by 177 days.

(21) Appl. No.: 15/109,943

(22) PCT Filed: Jan. 19, 2015

(86) PCT No.: PCT/JP2015/051248
§ 371 (c)(1),
(2) Date: Jul. 6, 2016

(87) PCT Pub. No.: WO2015/108186
PCT Pub. Date: Jul. 23, 2015

(65) Prior Publication Data
US 2016/0341691 A1    Nov. 24, 2016

(30) Foreign Application Priority Data
Jan. 17, 2014 (JP) .................................. 2014-006373

(51) Int. Cl.
*G01N 27/28* (2006.01)
*G01N 27/403* (2006.01)
(Continued)

(52) U.S. Cl.
CPC ........... *G01N 27/419* (2013.01); *G01N 27/41* (2013.01)

(58) Field of Classification Search
CPC .... G01N 27/28; G01N 27/403; G01N 27/406; G01N 27/4067; G01N 27/407;
(Continued)

(56) References Cited

U.S. PATENT DOCUMENTS 6,287,439 B1   9/2001  Kato et al.
6,533,911 B1 * 3/2003  Fujita ................. G01N 27/4075
                                                            204/424

(Continued)

FOREIGN PATENT DOCUMENTS

JP    11-118758    4/1999
JP    2001-165900  6/2001
JP    2003-166973  6/2003

*Primary Examiner* — Susan D Leong
(74) *Attorney, Agent, or Firm* — Nixon & Vanderhye PC (57) ABSTRACT

Provided is a gas sensor element that can increase detection accuracy of a specific gas component concentration by means of a sensor cell by reflecting changes in the operating temperature of a gas sensor element. The gas sensor element is provided with a solid electrolyte body having oxygen ion conductivity, a heater stacked to the solid electrolyte body via a reference gas space, a pump cell adjusting oxygen concentration in a measuring gas space, a sensor cell detecting specific gas component concentration in the measuring gas space, and an electronic conduction detector cell detecting current resulting from electronic conduction due to the heater. The electronic conduction detector cell includes an electronic conductor electrode which is provided to a measuring gas side surface of the solid electrolyte body and covered with an insulator.

7 Claims, 9 Drawing Sheets

(51) Int. Cl.
  *G01N 27/406* (2006.01)
  *G01N 27/407* (2006.01)
  *G01N 27/419* (2006.01)
  *G01N 27/41* (2006.01)

(58) Field of Classification Search
  CPC .......... G01N 27/4071; G01N 27/4074; G01N 27/4075; G01N 27/409; G01N 27/41
  See application file for complete search history.

(56) References Cited

U.S. PATENT DOCUMENTS

| | | | | |
|---|---|---|---|---|
| 6,554,983 B2 * | 4/2003 | Imamura | ............. | G01N 27/419 204/425 |
| 2001/0000598 A1 * | 5/2001 | Miyata | ............... | G01N 27/4074 205/780.5 |
| 2002/0104758 A1 | 8/2002 | Mizutani et al. | | |
| 2002/0162743 A1 * | 11/2002 | Inagaki | ............. | G01N 27/4065 204/425 |
| 2009/0250344 A1 | 10/2009 | Ohya et al. | | |

* cited by examiner

GAS SENSOR ELEMENT

CROSS-REFERENCE TO RELATED APPLICATION

This application is the U.S. national phase of International Application No. PCT/JP 2015/051248 filed 19 Jan. 2015, which designated the U.S. and claims the benefit of priority from earlier Japanese Patent Application No. 2014-006373 filed Jan. 17, 2014, the description of each of which are hereby incorporated herein by reference.

BACKGROUND

Technical Field

The present invention relates to a gas sensor element detecting the concentration of a specific gas component in a measuring gas.

Background Art

Gas sensor elements detecting the concentration of a specific gas component are typically disposed in a site where an exhaust gas is emitted, such as in an exhaust pipe of an engine, to detect the concentration of nitrogen oxide (NOx), hydrocarbon (HC) or the like contained in the exhaust gas as a measuring gas.

For example, in the gas sensor element of PTL 1, a pair of electrodes are provided to a solid electrolyte body to form an oxygen pump cell, an oxygen monitor cell and a sensor cell. The gas sensor element detects the concentration of a specific gas component in a measuring gas introduced into the inner space thereof. The gas sensor element of PTL 1 aims to detect the concentration of a specific gas component without being affected by the oxygen concentration in the inner space. To this end, the ends of an electrode of the oxygen monitor cell and an electrode of the sensor cell, the ends being located upstream of a gas stream, are ensured to be equally distanced from a gas inlet through which a measuring gas is introduced into the inner space.

CITATION LIST

Patent Literature

[PTL 1] JP-A-2002-310987

SUMMARY

The electric currents flowing between the pairs of electrodes configuring the oxygen pump cell, the oxygen monitor cell and the sensor cell are affected by the electronic conduction due to a heater which heats the gas sensor element. The electric currents which are caused by the electronic conduction to flow between the pairs of electrodes tend to increase with the increase of the operating temperature of the gas sensor element heated by the heater.

The heat quantity from the heater is controlled on the basis of the magnitude such as of the resistance between the pair of electrodes in the oxygen pump cell, such that the operating temperature of the gas sensor element is kept constant. However, the electrode contacting the measuring gas is deteriorated with time. The deterioration of the electrode results in increase such as of resistance between the pair of electrodes. In response to this, the heat quantity from the heater is increased. Accordingly, the operating temperature of the gas sensor element rises as the duration of using the gas sensor element becomes longer, which tends to increase the electric current which is caused by the electronic conduction to flow between the pair of electrodes.

The oxygen monitor cell shown in PTL 1, for example, simultaneously detect both of an oxygen ion current due to residual oxygen in a measuring gas and an electric current caused by the electronic conduction. Accordingly, the oxygen monitor cell cannot perform detection, with discrimination of the electric current caused by electronic conduction, from the oxygen ion current due to residual oxygen. Therefore, depending on the oxygen monitor cell, it is difficult to improve accuracy of detecting the concentration of a specific gas component by means of the sensor cell, when the operating temperature of the gas sensor element has changed.

The present invention has been made in light of the background set forth above, and has an object to provide a gas sensor element which can reflect change in the operating temperature of the gas sensor element to improve accuracy of detecting the concentration of a specific gas component by means of a sensor cell.

In an aspect of the present invention, a gas sensor element includes a solid electrolyte body, a measuring gas space, a reference gas space, a heater, a sensor cell and an electronic conduction detector cell. The solid electrolyte body has oxygen ion conductivity. The measuring gas space is formed on one of surfaces of the solid electrolyte body. A measuring gas which has passed through a diffusion resistor is introduced into the measuring gas space. The reference gas space is formed on the other surface of the solid electrolyte body, for introduction of a reference gas into the reference gas space. The heater heats the solid electrolyte body. The sensor cell detects the concentration of a specific gas component of the measuring gas space. The electronic conduction detector cell detects an electric current which is caused by electronic conduction to flow through the solid electrolyte body.

The gas sensor element includes the electronic conduction detector cell detecting intensity of electronic conduction caused by the heater. Accordingly, heat quantity from the heater and further the operating temperature of the gas sensor element can be detected by detecting the electric current which is caused by the electronic conduction to flow in the electronic conduction cell. Further, according to the electronic conduction detector cell, the electric current caused by electronic conduction, which increases when the gas sensor element has been deteriorated with time, can also be detected.

Thus, the sensor cell can detect the concentration of a specific gas component, with the change in operating temperature of the gas sensor element being reflected, by subtracting an electric current in the electronic conduction detector cell from an electric current detected in the sensor cell. It should be noted that the value of an electric current detected by the sensor cell corresponds to a sum of an oxygen ion current for detecting the concentration of a specific gas component and an electric current caused by electronic conduction.

Therefore, the gas sensor element can improve accuracy of detecting the concentration of a specific gas component by means of the sensor cell, with the change in operating temperature of the gas sensor element being reflected.

DETAILED DESCRIPTION OF PREFERRED EMBODIMENTS

Hereinafter are described preferred embodiments of the gas sensor element described above.

In the gas sensor element, an electronic conduction electrode has a surface at least exposed to a measuring gas. The exposed surface may be made of an electrode material inactive to (i.e., having less or no catalytic activity to, or which does not catalyze) decomposition of oxygen in the measuring gas.

In this case, an electronic conduction detector cell can be readily formed by appropriately choosing the material for the electronic conduction electrode. The electronic conduction electrode may be entirely made of the electrode material inactive to decomposition of oxygen in the measuring gas the material, or a surface layer of the electronic conduction electrode may be made of the material.

Materials that can be used for the electrode material include, for example, gold materials, silver materials, copper materials, lead materials, and the like.

The electronic conduction electrode has a measuring gas space side surface which may be covered with a coating layer which is impermeable to oxygen component of the measuring gas.

In this case, the coating layer can be provided, with the electronic conduction electrode being made of an ordinarily-used electrode material, thereby facilitating formation of the electronic conduction detector cell.

The solid electrolyte body has a measuring gas space side surface provided with the pump electrode in a longitudinal direction in which the sensor electrode and an electronic conductor electrode are arranged, the pump electrode being arranged upstream of a measuring gas stream, relative to the sensor electrode and the electronic conduction electrode. The sensor electrode and the electronic conduction electrode may be arranged keeping the same distance from the position of the pump electrode in the longitudinal direction.

In this case, since the pump electrode is provided to the solid electrolyte body to which the sensor electrode and the electronic conduction electrode are provided, it is easy for the heater to heat the pump electrode. Further, the sensor electrode and the electronic conduction electrode can be equally distanced from the heating center of the heater. With this configuration, the electric current caused by the electronic conduction due to the heater and flowing through the sensor electrode and the electronic conduction electrode can be ensured to be of the same level. Accordingly, accuracy of detecting the concentration of a specific gas component by means of the sensor cell can further be improved.

The gas sensor element includes a monitor cell including a monitor electrode which is provided to a measuring gas space side surface of the solid electrolyte body, where the sensor electrode and the electronic conduction electrode are provided. Further, the sensor electrode, the electronic conduction electrode and the monitor electrode are arranged keeping the same distance from the pump electrode in the longitudinal direction. The monitor cell may be configured to detect the oxygen concentration in the measuring gas space on the basis of the oxygen ion current passing between the monitor electrode and the reference electrode.

In this case, the sensor electrode, the electronic conduction electrode, and the monitor electrode can be equally distanced from the heating center to equalize the electric current caused by the electronic conduction due to the heater and flowing through these electrodes. Accordingly, the accuracy of detecting the concentration of a specific gas component by means of the sensor cell can further be improved.

The sensor electrode is made of an electrode material which is active to (i.e., which has catalytic activity to or can catalyze) decomposition of a specific gas component of the measuring gas, while the monitor electrode is made of an electrode material which is inactive to decomposition of a specific gas component (NOx or the like) in the measuring gas. The sensor cell detects an oxygen ion current according to an oxygen concentration and the concentration of a specific gas component. On the other hand, the monitor cell detects an oxygen ion current according to an oxygen concentration. The gas sensor element detects the concentration of a specific gas component of the measuring gas by subtracting an electric current detected by the monitor cell from an electric current detected by the sensor cell. If the gas sensor element has been deteriorated with time, the oxygen ion current due to the residual oxygen in the measuring gas can adversely affect the sensor cell's detecting the concentration of a specific gas component. In such a case, however, use of the monitor cell can correct the adverse effects.

It should be noted that the electric current value detected by each of the sensor cell and the monitor cell corresponds to a sum of an oxygen ion current for detecting the concentration of a specific gas component and an electric current caused by electronic conduction.

The effects of the electronic conduction due to the heater, on the sensor cell and the monitor cell can be corrected by the electronic conduction detector cell. Specifically, when the gas sensor element has been deteriorated with time, the sensor cell can detect the concentration of a specific gas component, taking account of the effects of the electronic conduction due to the heater in the case where heat quantity of the heater is increased.

Further, when detecting the concentration of a specific gas component, an oxygen ion current due to residual oxygen can be discriminated from an electric current due to electronic conduction.

The heater includes a conductor layer generating heat with energization, and insulator layers sandwiching the conductor layer therebetween. In this case, it may be so configured that the conductor layer is energized such that the electric current detected by the electronic conduction detector cell is kept constant.

The electric current caused by electronic conduction and flowing through the electronic conduction detector cell is correlated to the operating temperature of the gas sensor element. The electronic conduction detector cell does not detect an oxygen ion current generated by decomposition of oxygen in the measuring gas. The electronic conduction electrode of the electronic conduction detector cell hardly suffers from deterioration with time which would be resulted from decomposition of an oxygen component of the measuring gas. Accordingly, by energizing the conductor layer such that the electric current detected by the electronic conduction detector cell is constant, the operating temperature of the gas sensor element can be controlled accurately.

EXAMPLES

With reference to the drawings, hereinafter are described Examples of the gas sensor element.

Example 1

Figure 1:
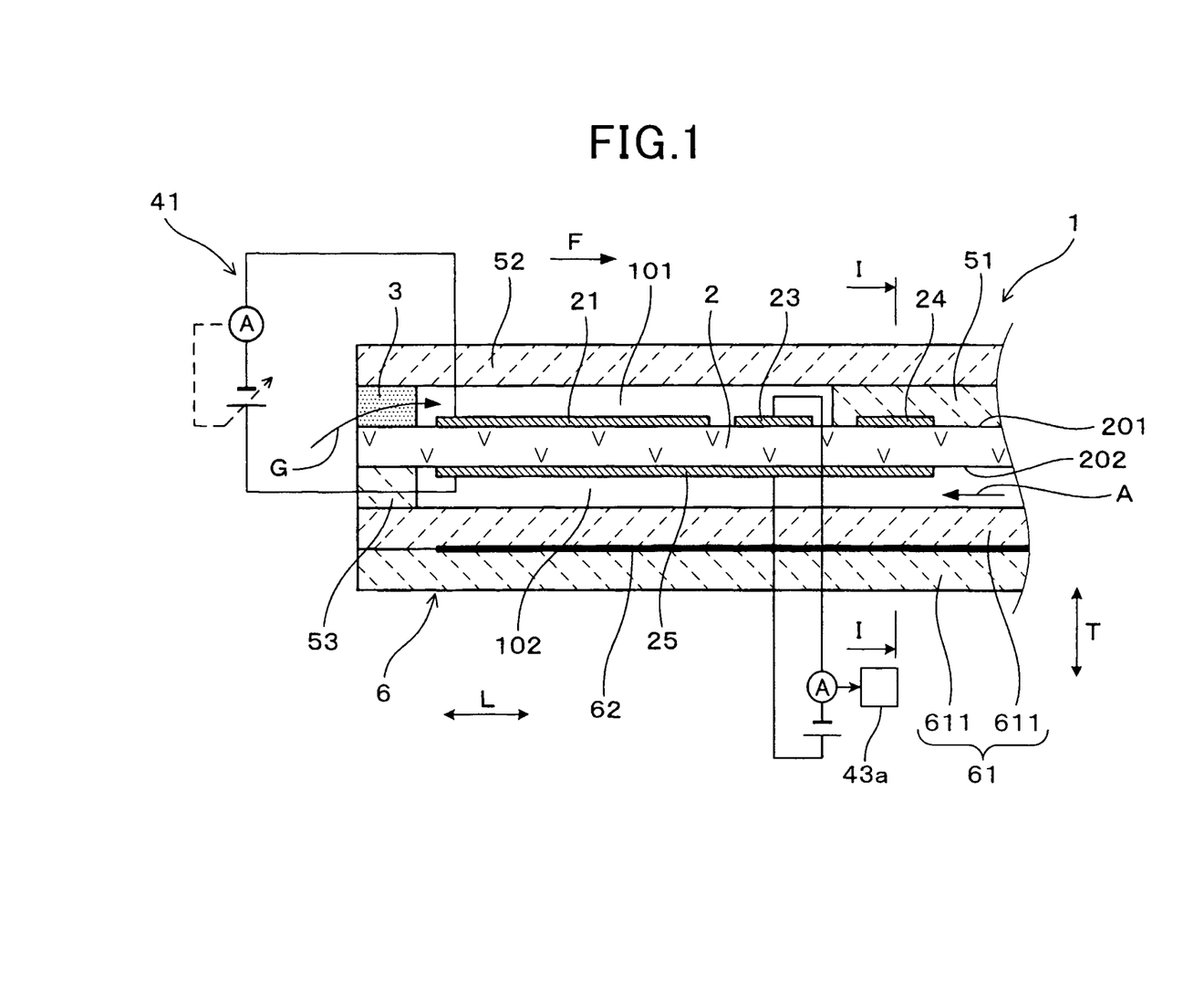
FIG. 1 is a cross-sectional view showing a gas sensor element, according to Example 1.
Figure 2:
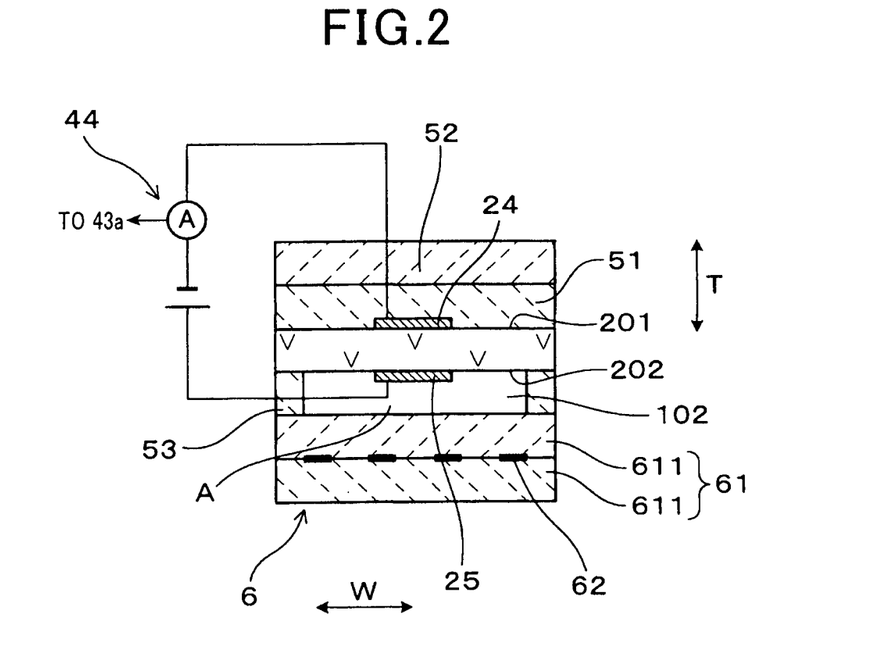
FIG. 2 is a cross-sectional view taken along the line I-I of FIG. 1, according to Example 1.

As shown in FIGS. 1 and 2, the gas sensor element 1 of the present example is provided with a solid electrolyte body 2, a measuring gas space 101, a reference gas space 102, a heater 6, a pump cell 41, a sensor cell 43 and an electronic conduction detector cell 44.

The solid electrolyte body 2 is made of materials having oxygen ion conductivity. In the present example, the solid electrolyte body is formed into a plate shape having a first surface and a second surface on the opposite side to the first surface. The measuring gas space 101 is formed on the first surface of the solid electrolyte body 2, being configured such that a measuring gas G which has passed through a diffusion resistor 3 is introduced therein. The reference gas space 102 is formed on the second surface of the solid electrolyte 2, being configured such that a reference gas A is introduced therein. The solid electrolyte body 2 has a reference gas space 102 side surface 202 (second surface) to which a reference electrode 25 is provided being exposed to the reference gas A.

As shown in FIGS. 1 and 2, the heater 6 is stacked on the solid electrolyte body 2 through the reference gas space 102. The pump cell 41 includes a pump electrode 21 which is provided to a measuring gas space 101 side surface (first surface) 201 of the solid electrolyte 2 and exposed to the measuring gas G. The pump cell 41 is configured to regulate the oxygen concentration in the measuring gas space 101 by applying a voltage across a pair of pump electrodes 21 and 25 sandwiching the solid electrolyte 2. The reference electrode 25 of the present example also serves as one of the pair of pump electrodes. The sensor cell 43 includes a sensor electrode 23 which is provided to the first surface 201 of the solid electrolyte body 2 and exposed to the measuring gas G. The sensor cell 43 is used for detecting the concentration of a specific gas component of the measuring gas space 101 on the basis of an oxygen ion current flowing between the sensor electrode 23 and the reference electrode 25. In the present example, the sensor cell 43 is provided with a calculator 43a. The calculator 43a calculates the concentration of a specific gas component on the basis of an electric current flowing between the sensor electrode 23 and the reference electrode 25, and an electric current caused by electronic conduction and detected by the electronic conduction detector cell 44 described below. The electronic conduction detector cell 44 has a pair of electronic conduction electrodes 24 and 25 which are provided on the first surface 201 and the second surface 202 of the solid electrolyte body 2 so as not to be exposed to the measuring gas G (i.e., so as to be blocked from the measuring gas G). In the present example, the reference electrode 25 configures one of the electronic conduction electrodes. The electronic conduction detector cell 44 is configured to detect the electric current caused by electronic conduction due to the heater 6 and flowing between the electronic conduction electrode 24 and the reference electrode 25.

Figure 3:
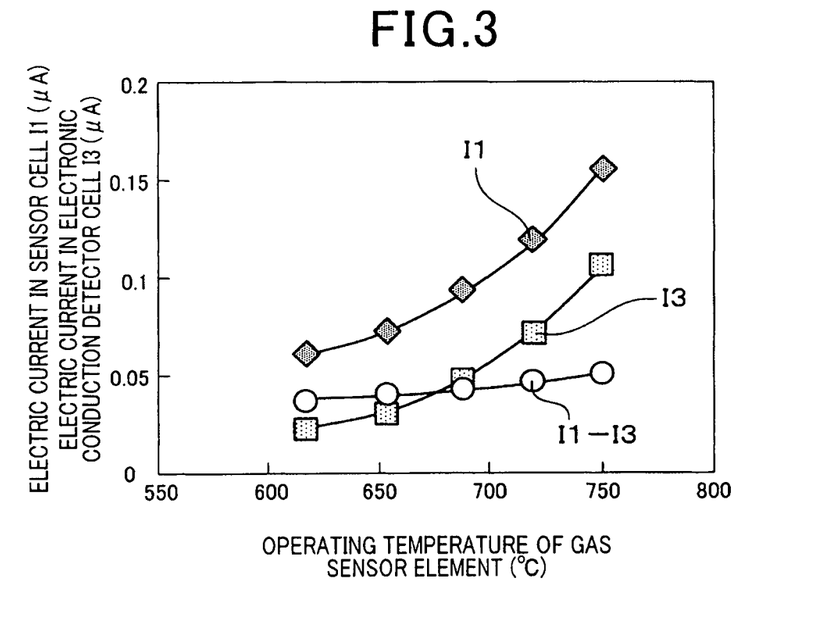
FIG. 3 is a chart showing a relationship between operating temperature and electric current, with the abscissa indicating the operating temperature of the gas sensor element, and the ordinate indicating the electric current passing through a sensor cell and an electronic conduction detector cell, according to Example 1.

With reference to FIGS. 1 to 3, hereinafter is described in detail the gas sensor element 1 of the present example.

The gas sensor element 1 of the present example, which is accommodated in a cover, is used being disposed in an exhaust pipe. The measuring gas G is an exhaust gas passing through the exhaust pipe, and the gas sensor element 1 is used for detecting the concentration of NOx (nitrogen oxide) as a specific gas component in the exhaust gas.

As shown in FIG. 1, the solid electrolyte body 2 is a substrate made of zirconia having oxygen ion conductivity. The pump electrode 21, the sensor electrode 23 and the electronic conduction electrode 24 are provided on the surface 201 of the solid electrolyte body 2 so as to have a constant thickness, the surface 201 being exposed to the measuring gas G. The reference electrode 25 is provided on the surface 202 of the solid electrolyte body 2 so as to have a constant thickness, the surface 202 being exposed to the reference gas A. The reference electrode 25 of the present example is provided to the solid electrolyte body 2 so as to entirely occupy the rear side of the area where the pump electrode 21, the sensor electrode 23 and the electronic conduction electrode 24 are positioned. Instead of providing a single reference electrode 25 relative to the pump electrode 21, sensor electrode 23 and electronic conduction electrode 24, three reference electrodes may be provided separately at the respective rear side positions of the pump electrode 21, the sensor electrode 23 and the electronic conduction electrode 24.

As shown in FIGS. 1 and 2, the diffusion resistor 3 and a first insulator 51 are stacked on the first surface 201 of the solid electrolyte body 2. In the diffusion resistor 3, small holes or the like are formed to limit diffusion of a measuring gas into the measuring gas space 101. The first insulator 51 is a plate-like substrate made of alumina. A second insulator 52 that is a plate-like substrate made of alumina is stacked on surfaces of the diffusion resistor 3 and the first insulator 51. The gas sensor element 1 has an end (first end) in a longitudinal direction L, from which the measuring gas G is introduced and at which the diffusion resistor 3 is disposed. The measuring gas G is introduced into the measuring gas space 101 through the diffusion resistor 3, and permitted to flow through the measuring gas space 101 in the longitudinal direction L. The first insulator 51 is provided to the first surface 201 of the solid electrolyte body 2 so as to occupy the other end (second end) of the gas sensor element in the longitudinal direction L and both ends of the gas sensor element in a width direction W, thereby surrounding the pump electrode 21 and the sensor electrode 23 from three directions.

The measuring gas space 101 is formed between the solid electrolyte body 2 and the second insulator 52, being enclosed, along four sides of the first surface 201 of the solid electrolyte body 2, by the diffusion resistor 3 and the first insulator 51. The measuring gas space 101 has a height T in a thickness direction perpendicular to the longitudinal direction L and the width direction W. The height T is constant in the areas where the pump electrode 21 and the sensor electrode 23 are provided.

As shown in FIGS. 1 and 2, a third insulator 53 which is a plate-like substrate made of alumina is stacked on the second surface 202 of the solid electrolyte body 2. The third insulator 53 is provided to the second surface 202 of the solid electrolyte body 2 so as to occupy the second end of the gas sensor element in the longitudinal direction L and both ends of the gas sensor element in the width direction W, thereby surrounding the reference electrode 25 from three directions. The reference gas space 102 is formed between the solid electrolyte body 2 and a fourth insulator 61, being enclosed, along three sides of the second surface 202 of the solid electrolyte body 2, by the third insulator 53, the three sides corresponding to the second end in the longitudinal direction L and both ends in the width direction W.

The heater 6 for heating the pump electrode 21 and the sensor electrode 23 is stacked on the third insulator 53. The heater 6 includes the fourth insulator 61 and a conductor layer 62. The fourth insulator 61 is stacked as an electrically insulating layer on the surface of the third insulator 53. The conductor layer 62 is provided to the fourth insulator 61, for energization. The fourth insulator 61 includes two electrically insulating plates 611 to sandwich the conductor layer 62 therebetween. The conductor layer 62 includes a pair of electrode portions and a heat generation portion. The electrode portions are connected to an external energizing means. The heat generation portion connects the pair of electrode portions to each other, and is energized when a voltage is applied across the pair of electrode portions to generate heat.

The fourth insulator 61 and the conductor layer 62 of the heater 6 are disposed parallel to the solid electrolyte body 2. The conductor layer 62 is disposed parallel to the pump electrode 21, the sensor electrode 23 and the electronic conduction electrode 24.

As shown in FIGS. 1 and 2, in the longitudinal direction L of the first surface 201 of the solid electrolyte body 2, in which the sensor electrode 23 and the electronic conduction electrode 24 are arranged, the pump electrode 21 is arranged upstream of the measuring gas G stream relative to the sensor electrode 23. A voltage application across the pump electrode 21 and the reference electrode 25 causes the pump cell 41 to pump oxygen out of or into the measuring gas space 101 through the solid electrolyte body 2. Thus, the pump cell 41 regulates the oxygen concentration in the measuring gas space 101 so as to be constant. It should be noted that the pump electrode 21 may be provided to another solid electrolyte body which is stacked on the solid electrolyte body 2 through an insulator to form the measuring gas space 101.

The sensor electrode 23 is made of an electrode material which is active to decomposition of NOx as a specific gas component of the measuring gas G. The sensor cell 43 detects the NOx concentration in the measuring gas G, on the basis of the value of oxygen ion current which flows between the sensor electrode 23 and the reference electrode 25 when NOx is decomposed.

The electronic conduction electrode 24 is disposed closer to the second end, in the longitudinal direction L, than the sensor electrode 23 is. The electronic conduction electrode 24 is covered with the first insulator 51 as a coating layer which is impermeable to (blocks) oxygen component of the measuring gas G. The electronic conduction electrode 24 of the present example is buried in the first insulator 51.

Next, advantageous effects of the gas sensor element 1 of the present example will be described.

The gas sensor element 1 of the present example includes the electronic conduction detector cell 44 detecting the magnitude of electronic conduction due to the heater 6. Accordingly, the heat quantity from the heater 6 and the operating temperature of the gas sensor element 1 can be detected by detecting the electric current caused by the electronic conduction. Further, the electronic conduction detector cell 44 can also detect the electric current caused by the electronic conduction which increases when the gas sensor element 1 has been deteriorated with time.

By subtracting an electric current in the electronic conduction detector cell 44 from an electric current detected in the sensor cell 43, the sensor cell 43 can detect the concentration of a specific gas component, reflecting change in the operating temperature of the gas sensor element 1. It should be noted that the value of the electric current detected in the sensor cell 43 corresponds to a sum of an oxygen ion current for detecting the concentration of a specific gas component and an electric current caused by electronic conduction.

Therefore, according to the gas sensor element 1 of the present example, change in the operating temperature of the gas sensor element 1 can be reflected in the detected concentration, which can increase detection accuracy of the concentration of a specific gas component.

FIG. 3 shows a relationship between operating temperature and electric current, with the abscissa indicating the operating temperature of the gas sensor element 1, and the ordinate indicating the electric current I1 flowing through the sensor cell 43 and the electric current I3 flowing through the electronic conduction detector cell 44. In this case, concentration of NOx as a specific gas component is taken to be 0 ppm. As shown in the figure, in both of the sensor cell 43 and the electronic conduction detector cell 44, the electric currents I1 and I3 increase as the operating temperature of the gas sensor element 1 increases. The electric currents I1 and I3 correlating to the operating temperature are caused mostly by the electronic conduction due to the heater 6. Accordingly, by subtracting the electric current I3 in the electronic conduction detector cell 44 from the electric current I1 in the sensor cell 43, the oxygen ion current generated by decomposition of NOx as a specific gas, can be detected as accurately as possible in the cell sensor 43.

In the longitudinal direction L of the gas sensor 1, there is a temperature distribution conforming to distances from the heating center of the heater 6. The distance from the sensor electrode 23 to the heating center of the heater 6 is shorter than the distance from the electronic conduction electrode 24 to the heating center of the heater 6. Therefore, the difference obtained by subtracting the electric current I3 in the electronic conduction detector cell 44 from the electric current I1 in the sensor cell 43 is not zero. The difference tends to increase with the increase in the operating temperature of the gas sensor element 1. Accordingly, the gas sensor element 1, when it is used, is calibrated in advance such that the difference is zero.

Example 2

The present example is different from Example 1 described above in that the position of the electronic conduction detector cell 44 has been changed.

Figure 4:
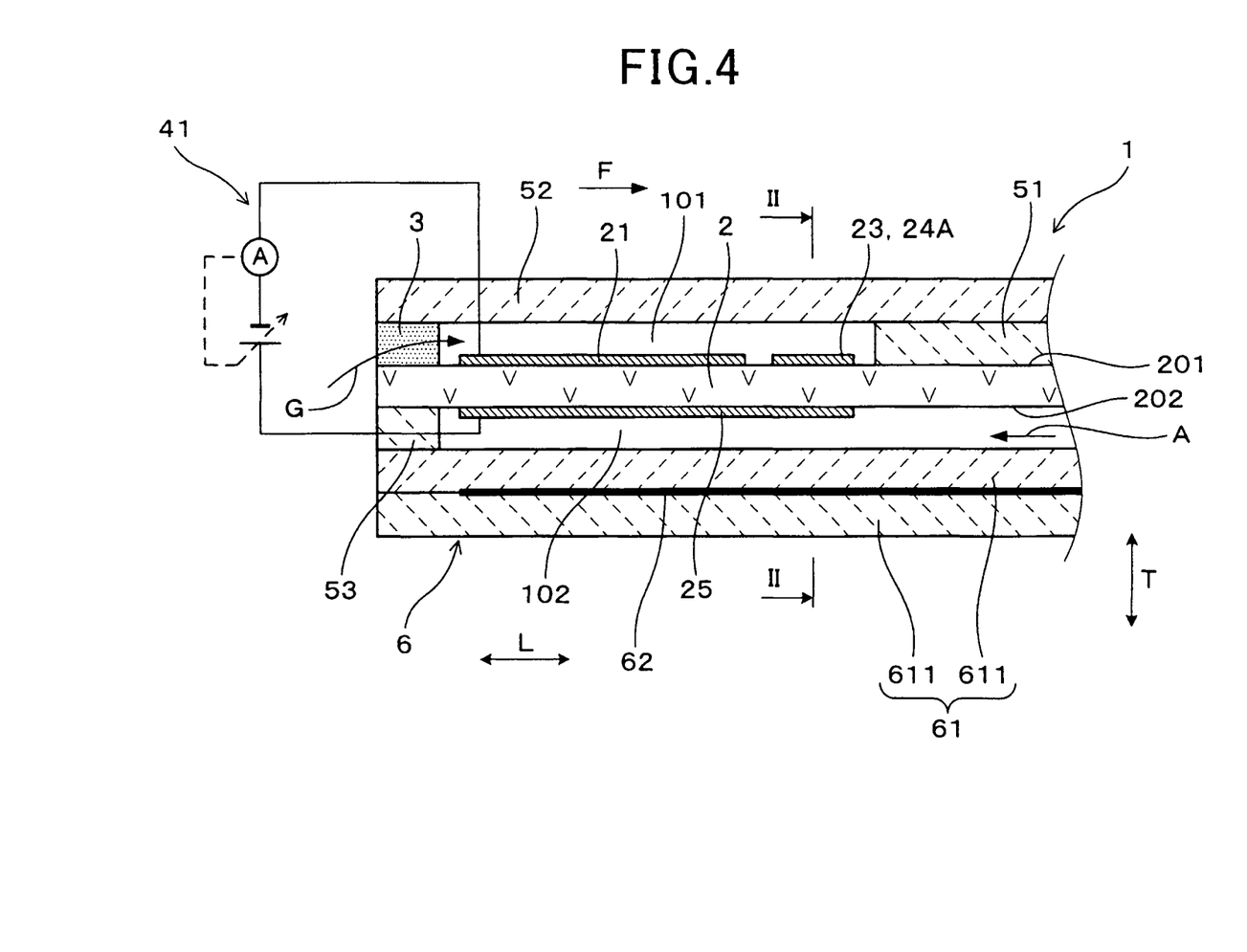
FIG. 4 is a cross-sectional view of a gas sensor element, according to Example 2.
Figure 5:
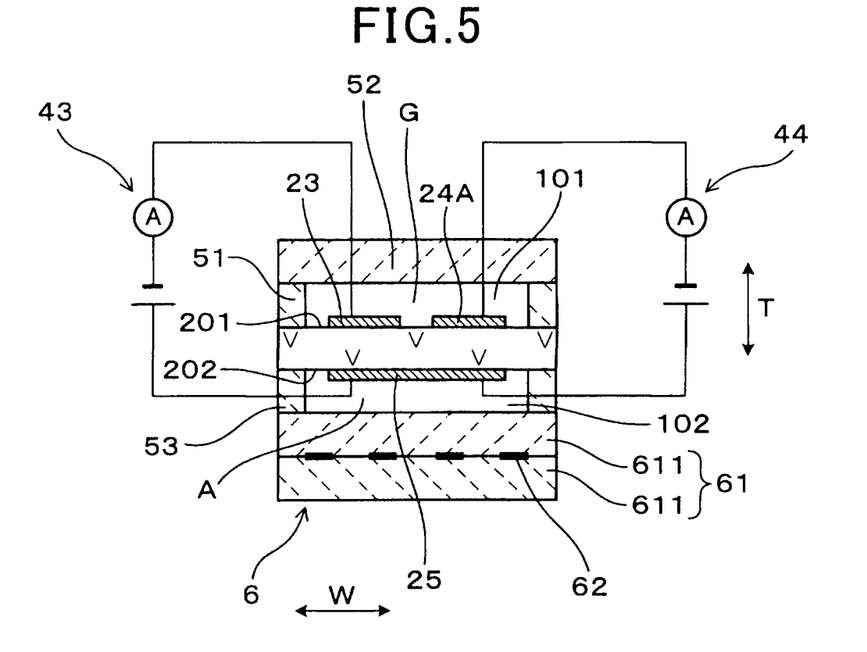
FIG. 5 is a cross-sectional view taken along the line II-II of FIG. 4, according to Example 2.

As shown in FIGS. 4 and 5, an electronic conduction electrode 24A of the electronic conduction detector cell 44 of the present example is formed on the first surface 201 of the solid electrolyte body 2 so as to be adjacent to the sensor electrode 23 of the sensor cell 43 in the width direction W which is perpendicular to the longitudinal direction L. The pump electrode 21, the sensor electrode 23 and the electronic conduction electrode 24A are disposed in the measuring gas space 101. The sensor electrode 23 and the electronic conduction electrode 24A are arranged being equally distanced from the position of the pump electrode 21, in the longitudinal direction L of the first surface 201 of the solid electrolyte 2. The electronic conduction electrode 24A is made of a gold material as an electrode material which is inactive to decomposition of oxygen in the measuring gas G. It should be noted that, in the electronic conduction electrode 24A, a surface exposed to the measuring gas G may be provided with a surface layer made of a gold material.

In the present example, the sensor electrode 23 and the electronic conduction electrode 24A can be equally distanced from the heating center of the heater 6 to equalize the electric currents caused by the electronic conduction due to the heater 6 and flowing through these electrodes 23 and 24A. This can further improve the accuracy in the sensor cell 43 detecting the concentration of a specific gas component.

In the present example, the rest of the configuration, including reference signs in the drawings, is similar to Example 1. Accordingly, advantageous effects similar to those of Example 1 can be obtained.

Figure 6:
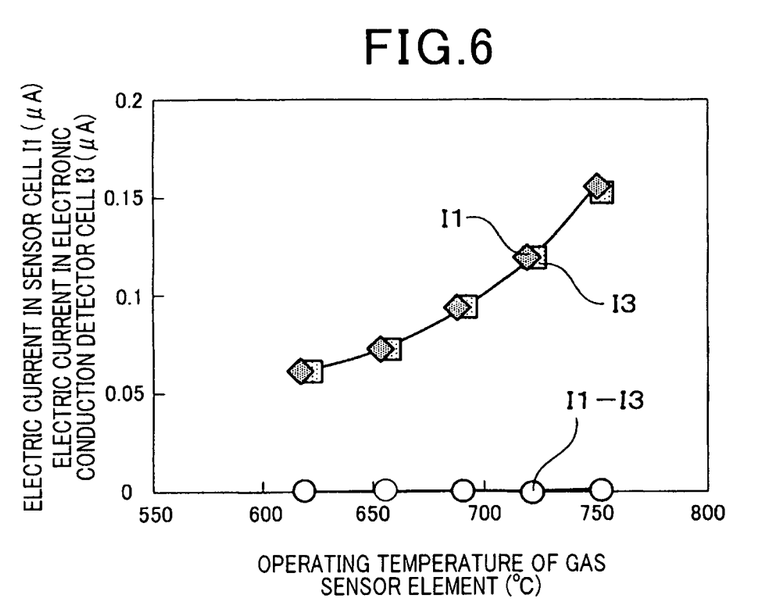
FIG. 6 is a chart showing a relationship between operating temperature and electric current, with the abscissa indicating the operating temperature of the gas sensor element, and the ordinate indicating the electric current passing through a sensor cell and an electronic conduction detector cell, according to Example 2.

Similar to FIG. 3 associated with Example 1, FIG. 6 shows a relationship of the operating temperature of the gas sensor element 1 with the electric currents I1 and I3 flowing through the sensor cell 43 and the electronic conduction detector cell 44, respectively. As will be understood from FIG. 6, the electric currents I1 and I3 increase in both of the sensor cell 43 and the electronic conduction detector cell 44, as the operating temperature of the gas sensor element 1 increases in accordance with the electronic conduction due to the heater 6. In the present example, it will be understood that, since the sensor electrode 23 and the electronic conduction electrode 24A are equally distanced from the heating center of the heater 6, there is no significant difference resulting from subtraction of the electric current I3 in the electronic conduction detector cell 44 from the electric current I1 in the sensor cell 43. Thus, as can be seen, the oxygen ion current in the sensor cell 43 can be detected more accurately.

Figure 7:
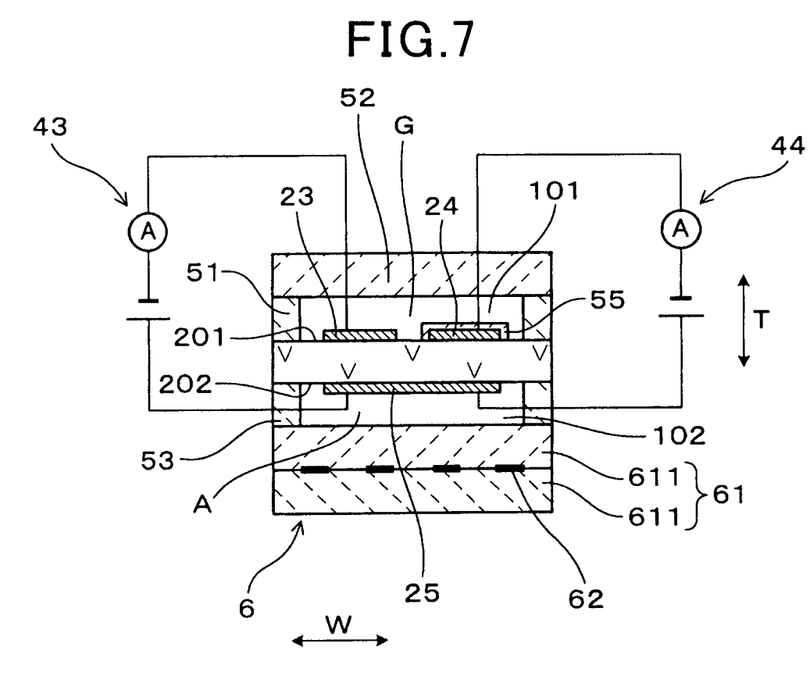
FIG. 7 is a view of another gas sensor element, according to Example 2, corresponding to the II-II cross section of FIG. 4.

As shown in FIG. 7, the electronic conduction electrode 24 may be covered with a coating layer 55 which is impermeable to oxygen component of the measuring gas G. The electronic conduction electrode 24 is disposed side-by-side with the sensor cell 43 in the width direction W in the measuring gas space 101, and covered with the coating layer 55 to prevent exposure to the measuring gas G. In this case, using a generally used platinum material or the like as the electrode material of the electronic conduction electrode 24, advantageous effects similar to those described above can be obtained. The thickness of the coating layer 55 can be made thinner as long as the impermeability to oxygen component of the measuring gas G is retained.

Example 3

In the present example, the gas sensor element 1 includes a monitor cell 42, in addition to the sensor cell 43 and the electronic conduction detector cell 44.

Figure 8:
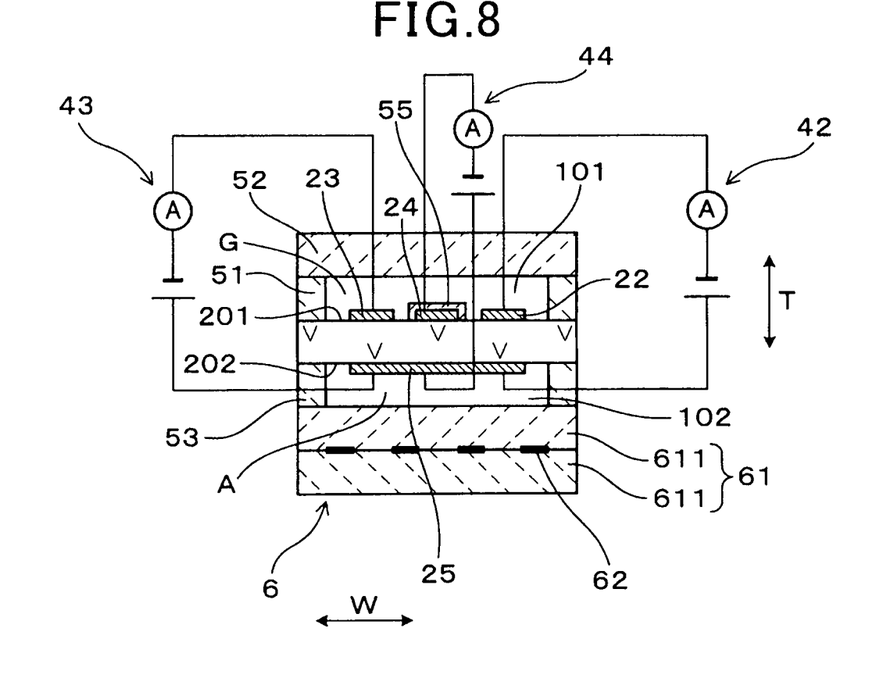
FIG. 8 is a view of a gas sensor element, according to Example 3, corresponding to the II-II cross section of FIG. 4.

As shown in FIG. 8, the monitor cell 42 includes a monitor electrode 22 provided to the first surface 201 of the solid electrolyte body 2 to which the sensor electrode 23 and the electronic conductor electrode 24 are provided. The monitor electrode 22 is formed on the first surface 201 of the solid electrolyte body 2 so as to be alongside the sensor electrode 23 and the electronic conduction electrode 24 in the width direction W perpendicular to the longitudinal direction L. The sensor electrode 23, the electronic conduction electrode 24 and the monitor electrode 22 are disposed in the measuring gas space 101. The sensor electrode 23, the electronic conduction electrode 24 and the monitor electrode 22 are arranged being equally distanced from the position of the pump electrode 21 in the longitudinal direction L of the first surface 201 of the solid electrolyte 2. Similar to FIG. 7 referred to in Example 2, the electronic conduction electrode 24 is covered with the coating layer 55 which is impermeable to the oxygen component of the measuring gas G. FIG. 8 is a diagram corresponding to the II-II cross section of FIG. 4 referred to in Example 2.

The monitor cell 42 is configured to detect oxygen concentration in the measuring gas space 101 on the basis of the oxygen ion current flowing between the monitor electrode 22 and the reference electrode 25.

The sensor electrode 23 is made of an electrode material which is active to decomposition of NOx as a specific gas component of the measuring gas G while the monitor electrode 22 is made of another electrode material which is inactive to decomposition of NOx of the measuring gas G. The sensor cell 43 detects an oxygen ion current, according to the oxygen concentration and the concentration of a specific gas component. On the other hand, the monitor cell 42 detects an oxygen ion current, depending on the oxygen concentration. The gas sensor element 1 subtracts an electric current detected in the monitor cell 42 from an electric current detected in the sensor cell 43 to detect the concentration of a specific gas component of the measuring gas G. When the gas sensor element 1 has been deteriorated with time, the oxygen ion current due to residual oxygen of the measuring gas G can adversely affect detection of NOx concentration performed by the sensor cell 43. However, use of the monitor cell 42 can correct such adverse effects. It should be noted that each of the current values detected by the sensor cell 43 and the monitor cell 42 corresponds to a sum of an oxygen ion current for detecting the concentration of a specific gas component and an electric current caused by electronic conduction.

The electronic conduction detector cell 44 can correct the adverse effects on the sensor cell 43 and the monitor cell 42 caused by electronic conduction due to the heater 6. Specifically, when the gas sensor element 1 has been deteriorated after long use, the amount of residual oxygen tends to increase in the measuring gas G after regulation of the oxygen amount by the pump cell 41. This is caused by lowering of the oxygen amount regulation ability of the pump cell 41, which is due to deterioration of the pump electrode 21 contacting the measuring gas G.

If the gas sensor element 1 has been deteriorated after long use and the pump electrode 21 has thus been deteriorated, there is an increase in the resistance between the pump electrode 21 and the reference electrode 25. The resistance tends to lower as the temperature rises. Accordingly, if the resistance increases with deterioration, the heat quantity of the heater 6 increases with the action of raising temperature of the gas sensor element 1. As a result, there is an increase in the electric current caused by electronic conduction due to the heater 6 in the cells 42, 43 and 44.

Figure 9:
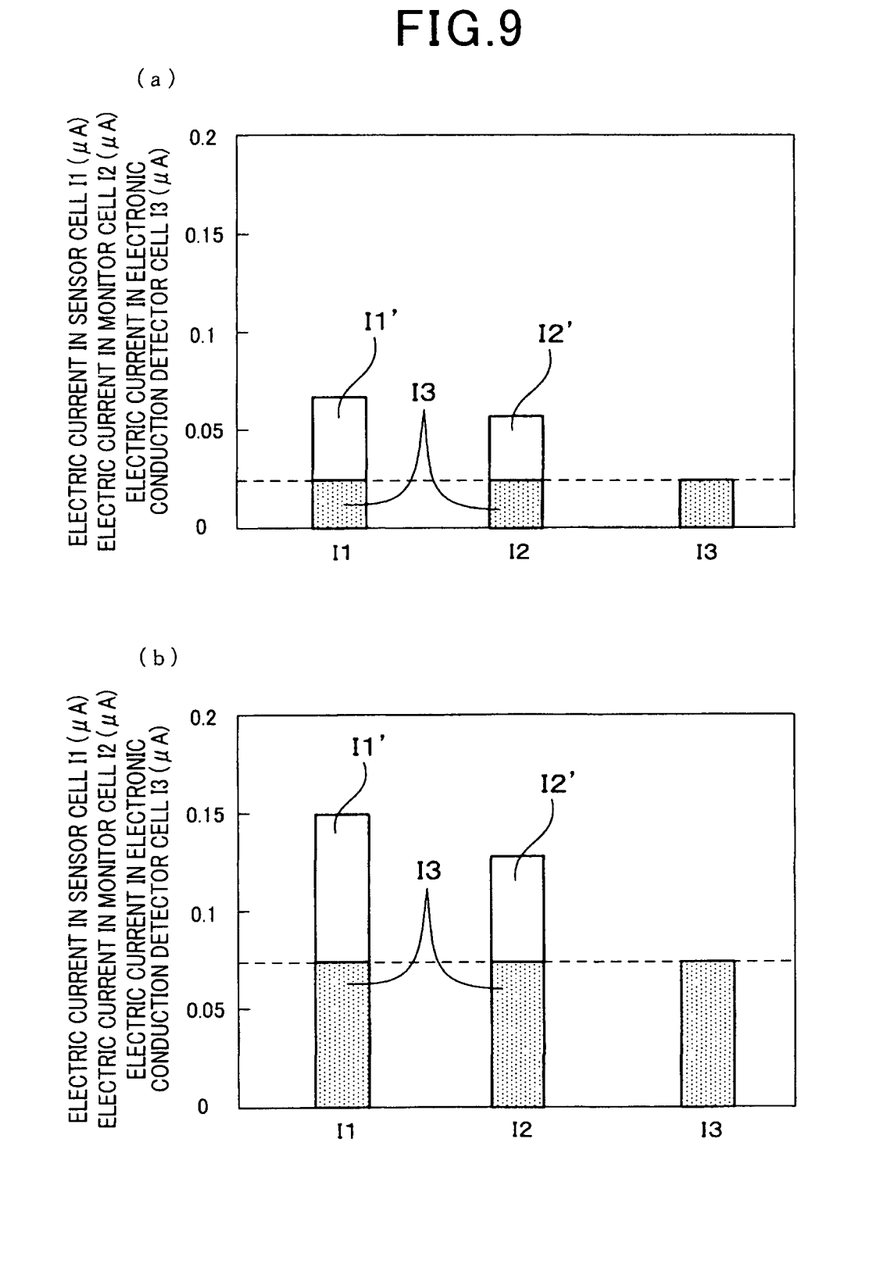
FIG. 9 is a set of charts each showing electric current passing through a sensor cell, a monitor cell and an electronic conduction detector cell, with (a) showing an initial state before deterioration of the gas sensor element and (b) showing an endurance state after deterioration of the gas sensor element.

FIG. 9 shows the electric currents I1, I2 and I3 flowing through the sensor cell 43, the monitor cell 42 and the electronic conduction detector cell 44, respectively, with (a) showing an initial state before deterioration of the gas sensor element 1, and (b) showing an endurance state after deterioration of the gas sensor element 1. In these states, concentration of NOx as a specific gas component is taken to be 0 ppm.

In both of the initial and endurance states, the electric current I3 caused by electronic conduction and the oxygen ion current I1' or I2' flow through the sensor cell 43 and the monitor cell 42, and only the electric current I3 caused by electronic conduction flows through the electronic conduction detector cell 44. The sensor electrode 23, the monitor electrode 22 and the electronic conduction electrode 24 are equally distanced from the heating center of the heater 6. Accordingly, in both of the initial and endurance states, an equal electric current I3 caused by electronic conduction passes through the cells 42, 43 and 44. The material used for the sensor electrode 23 easily causes decomposition of oxygen, compared to the material used for the monitor electrode 22. Accordingly, if the NOx concentration is 0 ppm, the oxygen ion current I1' flowing through the sensor cell 43 is larger than the oxygen ion current I2' flowing through the monitor cell 42.

As can be seen, the oxygen ion currents I1' and I2' in the sensor cell 43 and the monitor cell 42 in the endurance state are increased, being affected by the increase of residual oxygen. The increase of the oxygen ion currents I1' and I2' can be handled by subtracting the value of the electric current I2' in the monitor cell 42 from the value of the electric current I1' in the sensor cell 43.

Further, as can be seen, the electric current I3 caused by electronic conduction and flowing through the cells 42, 43 and 44 increases in the endurance state compared to the initial state, with the increase of heat quantity of the heater 6 due to deterioration of the pump electrode 21. The increase of electric current I3 caused by electronic conduction can be detected on the basis of the increase of electric current I3 in the electronic conduction cell.

The sensor cell 43 and the monitor cell 42 in the endurance state are capable of discriminating the change in the oxygen ion currents I1' and I2' due to lowering of the ability of the pump cell 41 regulating the oxygen amount, from the change in the electric current I3 due to electronic conduction which is caused by the increase in heat quantity of the heater 6 attributed to deterioration of the pump electrode 21. Especially, the degree of increase in the operating temperature of the gas sensor element 1 and the degree of deterioration of the pump electrode 21 can be comprehended by monitoring the amount of increase of the electric current I3 caused by electronic conduction. This enables detection of influences of operating temperature and deterioration, on the accuracy of detecting NOx concentration performed by the sensor cell 43 and the monitor cell 42. Accordingly, the gas sensor element 1 of the present example can learn the change in the operating temperature to thereby accurately detect NOx concentration.

In the present example, the rest of the configuration, including reference signs in the drawings, is similar to Examples 1 and 2. Accordingly, advantageous effects similar to those of Examples 1 and 2 can be obtained.

Failures (abnormalities in temperature, pump cell ability etc.) of the gas sensor element 1 can also be diagnosed by monitoring the amount of change in the electric current I3 flowing through the electronic conduction detector cell 44.

The amount of the electric current I3 due to electronic conduction cannot be detected without using the electronic conduction detector cell and only by using the sensor cell 43 and the monitor cell 42. Use of the electronic conduction detector cell 44 is needed to comprehend the amount of the electric current I3 due to electronic conduction.

Example 4

The present example is configured to energize a conductor layer 62 of the heater 6 such that the electric current detected by the electronic conduction detector cell 44 is constant.

The electric current caused by electronic conduction and flowing through the electronic conduction detector cell 44 is correlated to the operating temperature of the gas sensor element 1. The electronic conduction detector cell 44 does not detect oxygen ion current generated by decomposition of oxygen in the measuring gas G. Thus, the electronic conduction electrode 24 of the electronic conduction detector cell 44 is hardly deteriorated with time due to decomposition of an oxygen component of the measuring gas G. Accordingly, when the conductor layer 62 is energized such that the electric current value detected by the electronic conduction detector cell 44 is constant, the operating temperature of the gas sensor element 1 can be accurately controlled.

In the present example, the rest of the configuration, including reference signs in the drawings, is similar to Examples 1 to 3. Accordingly, advantageous effects similar to those of Examples 1 to 3 can be obtained.

REFERENCE SIGNS LIST

1 Gas sensor element
101 Measuring gas space
102 Reference gas space
2 Solid electrolyte body
21 Pump electrode
23 Monitor electrode
24 Electronic conduction electrode
3 Diffusion resistor
41 Pump cell
42 Monitor cell
43 Sensor cell
44 Electronic conduction detector cell
6 Heater
G Measuring gas
A Reference gas

The invention claimed is:
1. A gas sensor element, comprising:
a solid electrolyte body having a first surface and a second surface and having oxygen ion conductivity;
a measuring gas which has passed through a diffusion resistor being introduced into a measuring gas space on the first surface of the solid electrolyte body;
a reference gas is introduced into a reference gas space on the second surface of the solid electrolyte body;
a heater stacked directly or indirectly on the solid electrolyte body;
a sensor cell including a sensor electrode provided to the first surface of the solid electrolyte body, for detecting a concentration of a specific gas component of the measuring gas space on the basis of an oxygen ion current flowing between the sensor electrode and a reference electrode, the reference electrode being provided to the second surface of the solid electrolyte body;
an electronic conduction detector cell including a pair of electronic conduction electrodes configured to detect an electric current which is caused by an electronic conduction based on heat from the heater and flowing between the pair of electronic conduction electrodes, the pair of electronic conduction electrodes being formed of the reference electrode and a second electrode provided on the first surface of the solid electrolyte body; and a pump cell including a pair of pump electrodes and applying a voltage across the pair of pump electrodes to regulate oxygen concentration in the measuring gas space, the pump electrodes being formed of the reference electrode and a third electrode provided on the first surface of the solid electrolyte body or on a surface of another solid electrolyte body stacked on the solid electrolyte body.

2. The gas sensor element according to claim 1, wherein one of the electronic conduction electrodes has a surface exposed at least to the measuring gas and made of an electrode material which is inactive to decomposition of oxygen in the measuring gas.

3. The gas sensor element according to claim 1, wherein one of the electronic conduction electrodes has a surface located on the measuring gas space side, the surface being covered with a coating layer which is impermeable to an oxygen component of the measuring gas.

4. The gas sensor element according to claim 1, wherein:

the first surface of the solid electrolyte body is provided with the pump electrode in a longitudinal direction in which the sensor electrode and one of the electronic conductor electrodes are arranged, the pump electrode being arranged upstream of the measuring gas stream relative to the sensor electrode and one of the electronic conduction electrodes; and the sensor electrode and one of the electronic conduction electrodes are arranged side by side in a width direction of the first surface, the width direction being perpendicular to the longitudinal direction.

5. The gas sensor element according to claim 4, wherein:

the gas sensor element further comprises a monitor cell including a pair of monitor electrodes provided on the first surface and the second surface of the solid electrolyte body to which the sensor electrode and one of the electronic conduction electrodes, respectively, are provided, the sensor electrode, one of the electronic conduction electrodes and the monitor electrode which are provided on the first surface of the solid electrolyte body are arranged side by side in the width direction, and the monitor cell is configured to detect an oxygen concentration in the measuring gas space on the basis of an oxygen ion current flowing between the pair of monitor electrodes.

6. The gas sensor element according to claim 1, wherein the heater includes a conductor layer energized to generate heat and insulator layers sandwiching the conductor layer therebetween, and is configured to energize the conductor layer according to an electric current detected by the electronic conduction detector cell.

7. The gas sensor element according to claim 1, wherein the sensor cell includes a calculator calculating a concentration of the specific gas component on the basis of an electric current flowing between the sensor electrodes electrode and the reference electrode and an electric current which is caused by the electronic conduction and detected by the electronic conduction detector cell.

* * * * *